US00PP13995P29

(12) United States Plant Patent
Strope

(10) Patent No.: US PP13,995 P2
(45) Date of Patent: Jul. 22, 2003

(54) NEW GUINEA IMPATIENS PLANT NAMED 'BALCELNEON'

(75) Inventor: Kerry Strope, Pismo Beach, CA (US)

(73) Assignee: Ball Flora Plant, a division of Ball Horticultural Co., West Chicago, IL (US)

( * ) Notice: Subject to any disclaimer, the term of this patent is extended or adjusted under 35 U.S.C. 154(b) by 0 days.

(21) Appl. No.: 10/115,049

(22) Filed: Apr. 1, 2002

(51) Int. Cl.[7] ..... A01H 5/00
(52) U.S. Cl. ..... Plt./318
(58) Field of Search ..... Plt./318

*Primary Examiner*—Bruce R. Campell
*Assistant Examiner*—Annette Para
(74) *Attorney, Agent, or Firm*—C. A. Whealy

(57) ABSTRACT

A new and distinct cultivar of New Guinea Impatiens plant named 'Balcelneon', characterized by its upright, rounded and uniform plant habit; red purple-colored flowers with a light pink-colored eye that are positioned above and beyond the leaves; and dark green-colored leaves.

1 Drawing Sheet

BOTANICAL CLASSIFICATION/CULTIVAR DENOMINATION

*Impatiens hawkeri* cultivar Balcelneon.

BACKGROUND OF THE INVENTION

The present Invention relates to a new and distinct cultivar of New Guinea Impatiens plant, botanically known as *Impatiens hawkeri,* and hereinafter referred to by the name 'Balcelneon'.

The new Impatiens is a product of a planned breeding program conducted by the Inventor in Arroyo Grande, Calif. The objective of the breeding program is to develop New Guinea Impatiens cultivars that have a freely branching growth habit and large flowers with attractive flower colors.

The new Impatiens originated from a cross-pollination made by the Inventor in 1998 of the *Impatiens hawkeri* cultivar Toga, disclosed in U.S. Plant Pat. No. 10,304, as the female, or seed parent, with the *Impatiens hawkeri* cultivar BFP-605 Orange, disclosed in U.S. Plant Pat. No. 10,078, as the male, or pollen parent. The cultivar Balcelneon was discovered and selected by the Inventor as a flowering plant within the progeny of the stated cross-pollination in a controlled environment in Arroyo Grande, Calif.

Asexual reproduction of the new cultivar by terminal cuttings taken in Arroyo Grande, Calif. since March, 1998, has shown that the unique features of this new Impatiens are stable and reproduced true to type in successive generations.

SUMMARY OF THE INVENTION

The following traits have been repeatedly observed and are determined to be the unique characteristics of 'Balcelneon'. These characteristics in combination distinguish 'Balcelneon' as a new and distinct Impatiens cultivar:

1. Upright, rounded and uniform plant habit.

2. Red purple-colored flowers with a light pink-colored eye that are positioned above and beyond the leaves.

3. Dark green-colored leaves.

Plants of the new Impatiens differ primarily from plants of the female and male parents in flower color.

Plants of the new Impatiens can be compared to plants of the cultivar BFP-844, disclosed in U.S. Plant Pat. No. 11,415. In side-by-side comparisons conducted in West Chicago, Ill., plants of the new Impatiens differed from plants of the cultivar BFP-844 in the following characteristics:

1. Plants of the new Impatiens were taller and more vigorous than plants of the cultivar BFP-844.

2. Plants of the new Impatiens had longer lateral branches and shorter internodes than plants of the cultivar BFP-844.

3. Plants of the new Impatiens had larger flowers than plants of the cultivar BFP-844.

4. Plants of the new Impatiens and the cultivar BFP-844 differed in flower color.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph differ from the color values cited in the detailed botanical description which accurately describe the colors of the new Impatiens. The photograph comprises a side perspective view of multiple flowering plants of 'Balcelneon' grown in a container.

DETAILED BOTANICAL DESCRIPTION

The cultivar Balcelneon has not been observed under all possible environmental conditions. The phenotype may vary somewhat with variations in environment such as temperature and light intensity without, however, any variance in genotype.

The aforementioned photograph and following observations and measurements describe plants grown in West Chicago, Ill., under commercial practice in a polycarbonate-covered greenhouse with day temperatures ranging from 20 to 24° C., night temperatures ranging from 16 to 20° C. and light levels ranging from 4,000 to 6,000 footcandles. Rooted young plants were planted in containers and had been growing for about eight weeks when the photographs and the description were taken.

In the following description, color references are made to The Royal Horticultural Society Colour Chart, 1995 Edition, except where general terms of ordinary dictionary significance are used.

Botanical classification: *Impatiens hawkeri* cultivar Balcelneon.

Parentage:

*Female parent.*—*Impatiens hawkeri* cultivar Toga, disclosed in U.S. Plant Pat. No. 10,304.

*Male parent.*—*Impatiens hawkeri* cultivar BFP-605 Orange, disclosed in U.S. Plant Pat. No. 10,078.

Propagation:

*Type cutting.*—Terminal cuttings.

*Time to initiate roots.*—About 7 days at 18° C.

*Time to produce a rooted cutting.*—About 21 days at 18° C.

*Root description.*—Fine, fibrous and white in color.

*Rooting habit.*—Freely branching.

Plant description:

*General appearance.*—Upright, rounded and uniform plant habit; freely basal branching growth habit, about five basal branches form per plant. Vigorous.

*Plant height.*—About 15.5 cm.

*Plant diameter or spread.*—About 25.1 cm.

*Lateral branches.*—Length: About 7.6 cm. Diameter: About 7 mm. Internode length: About 2.2 cm. Color: 146B overlain with 173A.

*Foliage description.*—Arrangement: Opposite or in whorls of three. Length: About 11.9 cm. Width: About 4 cm. Shape: Elliptic. Apex: Acuminate. Base: Attenuate. Margin: Serrulate with ciliation. Texture, upper surface: Smooth, glabrous. Texture, lower surface: Sparse pubescence along veins. Venation pattern: Pinnate. Color: Young and fully expanded foliage, upper surface: Slightly more yellow than 139A. Young and fully expanded foliage, lower surface: 139C. Venation, upper surface: 145C. Venation, lower surface: 173B. Petiole: Length: About 1.8 cm. Diameter: About 3 mm. Texture, upper and lower surfaces: Smooth, glabrous. Color, upper and lower surfaces: 145C overlain with 178A.

Flower description:

*Flower type and flowering habit.*—Single rounded flowers. Usually about six flowers and flower buds per lateral branch. Flowers positioned above and beyond the foliage and typically face upward or outward. Flowers not fragrant. Petals self-cleaning; gynoecium persistent.

*Flower longevity.*—Flowers last about one week on the plant.

*Flowering season.*—Year-round under greenhouse conditions; in the garden, flowering from spring until fall. Plants begin flowering about eight weeks after planting.

*Flower buds.*—Length: About 1.9 cm. Diameter: About 1.1 cm. Shape: Ovoid. Color: 52A.

*Flower diameter.*—About 6.8 cm.

*Flower depth.*—About 1.5 cm.

*Flower shape.*—Rounded; mostly flat.

*Petals.*—Quantity: Five per flower, imbricate. Length, banner petal: About 3.4 cm. Length, lateral and basal petals: About 3.6 cm. Width, banner petals: About 4.5 cm. Width, lateral and basal petals: About 3.1 cm. Shape: Obovate. Apex: Emarginate. Base, banner petal: Truncate. Base, lateral and basal petals: Attenuate. Margin: Entire. Texture, upper and lower surfaces: Smooth; satiny. Color: When opening and fully opened, upper surface: 58B; towards base, 58D to 56D; at base, 57A. When opening and fully opened, lower surface: 52B.

*Spur.*—Quantity: One per flower. Length: About 6.4 cm. Diameter, at apex: Less than 1 mm. Diameter, at flower: About 2.5 mm. Aspect: Curved downward. Color: 53B.

*Peduncles.*—Length: About 6.6 cm. Diameter: About 1 mm. Strength: Strong; flexible. Angle: Acute. Color: 145C overlain with 178A.

*Reproductive organs.*—Androecium: Stamen quantity/arrangement: Five fused at anthers, hooded; filaments free. Anther length: About 2 mm. Anther shape: Oval. Anther color: 13C. Pollen amount: Abundant. Pollen color: 12D. Gynoecium: Pistil quantity: One per flower. Pistil length: About 6 mm. Stigma color: Colorless. Style length: Less than 1 mm. Style color: 150D. Ovary arrangement: Five-celled. Ovary color: 144A.

*Seeds/fruits.*—Seed and fruit development has not been observed.

Disease/pest resistance: Plants of the new Impatiens have not been observed to be resistant to pathogens and pests common to Impatiens.

It is claimed:

1. A new and distinct cultivar of New Guinea Impatiens plant named 'Balcelneon', as illustrated and described.

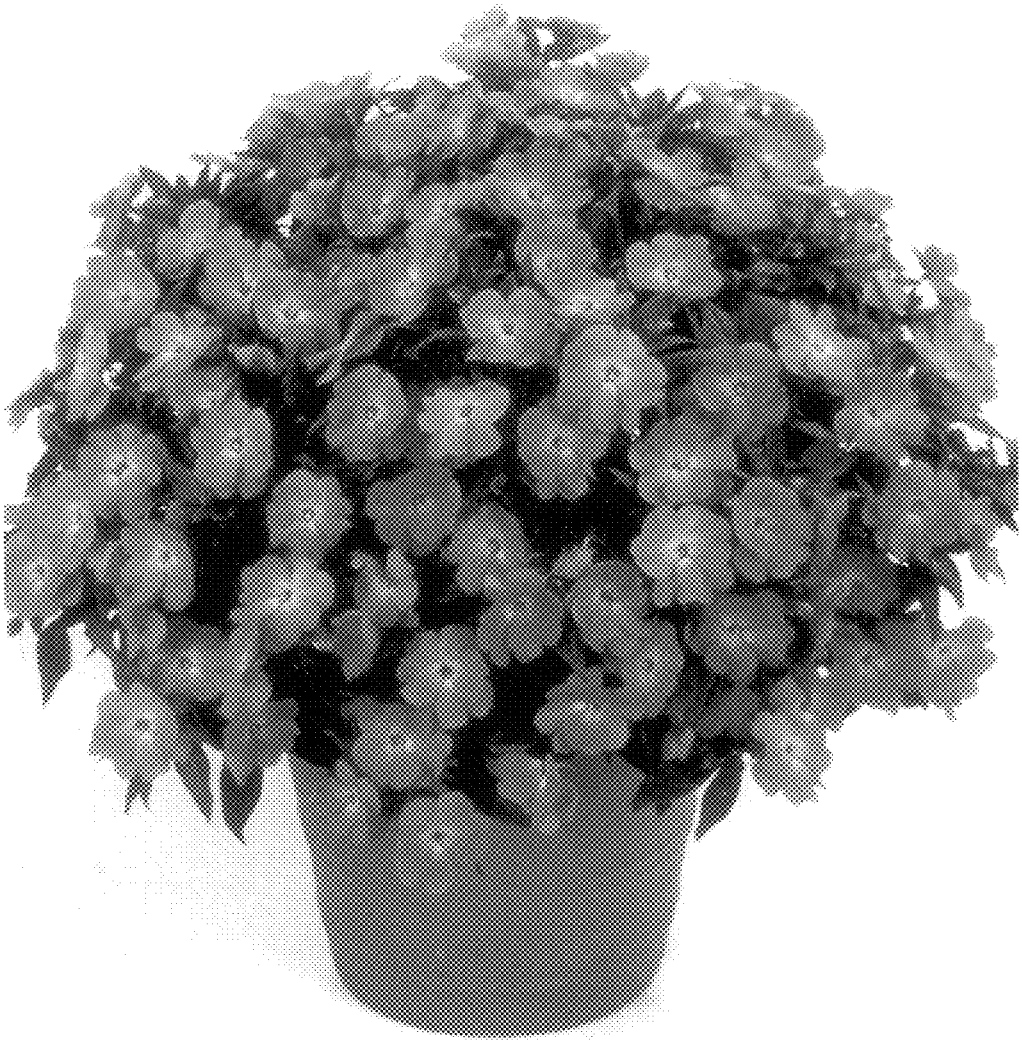

* * * * *